(12) United States Patent
Fifolt et al.

(10) Patent No.: US 6,303,812 B1
(45) Date of Patent: Oct. 16, 2001

(54) ISOLATION OF PRODUCTS FROM SELECTIVE DEHALOGENATION OF HALOAROMATICS

(75) Inventors: Michael J. Fifolt, Grand Island; Michael C. Savidakis, Niagara Falls; Ronald Spohn, Getzville; Daniel R. Thielen, Snyder; William S. Derwin, Grand Island; David C. Johnson, Cheektowaga, all of NY (US)

(73) Assignee: Occidental Chemical Corporation, Dallas, TX (US)

( * ) Notice: Subject to any disclaimer, the term of this patent is extended or adjusted under 35 U.S.C. 154(b) by 0 days.

(21) Appl. No.: 09/504,403

(22) Filed: Feb. 15, 2000

(51) Int. Cl.$^7$ .................................................. C07C 69/76
(52) U.S. Cl. ........................... 560/103; 562/45; 562/493; 564/184; 568/323; 558/411
(58) Field of Search ................................ 560/103; 562/45, 562/493; 564/184; 568/323; 558/411

(56) References Cited

U.S. PATENT DOCUMENTS 5,886,210   3/1999   Rayle .

Primary Examiner—Paul J. Killos

(74) Attorney, Agent, or Firm—Richard D. Fuerle; Anne E. Brookes

(57) ABSTRACT

Disclosed is a method of isolating the aromatic product formed when a substrate having the general formula

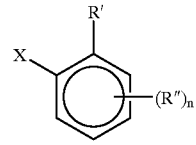

is dehalogenated, forming a product mixture of copper salts and aromatic product, where X is the halogen removed from the substrate to form the aromatic product, R' is COOH, COOR, COR, CN, COH(R)$_2$, or SO$_3$H, each R" is independently selected from halogen, R, or OR or two vicinal R" groups form one or more fused aromatic rings, R is alkyl from C$_1$ to C$_{18}$ or aryl from C$_6$ to C$_{18}$, and n is 1 to 4. Water in an amount about 1 to about 5 times the amount of the substrate is added to the product mixture, forming an organic phase that contains the aromatic product and an aqueous phase that contains the copper salts. If the density of the organic phase differs from the density of said aqueous phase by less than 0.1 g/cc, a suitable solvent is added to the product mixture in an amount sufficient to increase the differences between the organic and aqueous phases to at least 0.1 g/cc. The organic phase can be separated from the aqueous phase by decantation.

20 Claims, No Drawings

ISOLATION OF PRODUCTS FROM SELECTIVE DEHALOGENATION OF HALOAROMATICS

BACKGROUND OF THE INVENTION

This invention relates to a method of isolating the products formed when certain haloaromatics are dehalogenated. In particular, it relates to the dilution of the reaction products with water to form separate phases followed by decantation.

In U.S. Pat. No. 5,886,210, Example 14(d), 2,3,5-trichloro4-methylmethylbenzoate (TCMMB) was mixed with elemental copper and propionic acid and reacted at about 130 to 135° C. to produce 3,5-dichloro4-methylmethylbenzoate (DCMMB). The product mixture was diluted with xylenes and filtered. The solids were washed with xylenes and the filtrates combined. The filtrates were washed with 1 M HCl and the product DCMMB was dried.

SUMMARY OF THE INVENTION

We have discovered that, under the conditions of this invention, adding water to a mixture containing a cuprous halide, a cuprous carboxylic acid salt, and certain dehalogenated aromatic products, such as DCMMB, will cause the mixture to separate into an organic phase containing the product and an aqueous phase containing copper salts; the two phases can be separated by decantation. (If the product has a high melting point, an inert solvent can be added to dissolve it prior to the addition of water to form the two phases.) This method of separating the components of the mixture is superior to the prior method because it is a simpler process since filtration is eliminated and usually no solvent is needed. For many purposes, the decanted product is sufficiently pure that it need not be distilled. Also, the copper in solution can be reduced to elemental copper and reused and the carboxylic acid can also be recovered.

DESCRIPTION OF THE PREFERRED EMBODIMENTS

Substrates useful in the dehalogenation reaction that forms the product mixture treated using the process of this invention have the general formula

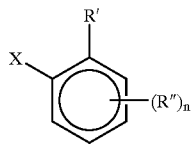

where X is the halogen to be removed to form the product, R' is COOH, COOR, COR, CN, COH(R)$_2$, or SO$_3$H, each R" is independently selected from halogen, R, or OR or two vicinal R" groups form one or more fused aromatic rings, R is alkyl from C$_1$ to C$_{18}$ or aryl from C$_6$ to C$_{18}$, and n is 1 to 4. Preferably, X is chlorine, R' is COOR, R is alkyl from C$_1$ to C$_4$ (most preferably methyl), R" is a halogen (preferably chlorine) and/or methyl, and n is 2 as those compounds are commercially more important. More preferably, at least one R" is a halogen (preferably chlorine) in the meta position as a solvent is usually not needed to dehalogenate those substrates. Examples of substrates useful in this invention include TCMMB, methyl-2,5-dichloro-4-methylbenzoate, 2,4-dichloroacetophenone, 2,5-dichlorobenzoic acid, methyl 2,5-dichlorobenzoate, 2,3-dichlorobenzoic acid, 2,5-dichlorobenzonitrile, and 2,5-dichlorobenzamide.

The elemental copper used in the dehalogenation reaction should be finely divided. About 1 to about 2.5 equivalents of copper should be used as less copper will leave too much unreacted substrate and more copper will leave too much unreacted copper. Preferably, about 1.7 to about 2.1 equivalents of copper are used.

Any carboxylic acid can be used in the dehalogenation reaction. Preferably, the carboxylic acid is a liquid at the reaction temperature. Examples of carboxylic acids that can be used include acetic acid, propionic acid, butyric acid, and benzoic acid. The preferred carboxylic acids are acetic acid and propionic acid as they are commercially available liquids and are not too malodorous. About 1.5 to about 3.5 equivalents of the carboxylic acid should be used per halogen to be removed as less is less effective and more is unnecessary and wasteful; preferably, about 1.9 to about 2.1 equivalents are used.

The dehalogenation reaction is best performed at or near the boiling point of the acid, but lower temperatures can be used if desired. For propionic acid, the temperature range can be about 100 to about 200° C., though about 140 to about 170° C. is preferred. The reaction normally requires about 2 to about 20 hours.

After the reaction is complete, the product mixture is cooled and water in an amount about 1 to about 5 times the weight of the substrate is added. Less water may not dissolve all the salts and more water is unnecessary. The preferred amount of water is about 1 to about 2 times the weight of the substrate. As an example, the product mixture can be cooled to about 80° C and hot water in an amount about equal to the substrate weight can be added so that the resulting temperature of the product mixture is about 40 to about 800° C.

If the product differs in density from the density of the aqueous solution formed by at least about 0.1 g/cc, then no solvent is needed and organic and aqueous phases will form, with the product in the organic phase and the copper salts in the aqueous phase. (If the product has a high melting point, a solvent can be used to dissolve it.) If the product is DCMMB and the carboxylic acid is propionic acid, the DCMMB will form a lower phase and the aqueous solution will form the upper phase. If the product does not differ in density from the density of the aqueous solution by at least about 0.1 g/cc, either a sufficient amount of a dense solvent, such as methylene chloride, chloroform, dichloroethane, or chlorobenzene, should be used so that the solution of the product is at least 0.1 g/cc denser than the aqueous solution, or a sufficient amount of a less dense solvent, such as hexane, toluene, or ethyl acetate, should be used so that the aqueous solution is at least 0.1 g/cc denser than the solution of the product. Alternatively, additional water may be added in order to lower the salt concentration in the aqueous phase, thus lowering its density. Preferably, the difference in densities should be at least about 0.2 g/cc so that the two phases form quickly.

The organic phase can be decanted and washed with water. The purity of the product in the organic phase may be high enough so that distillation is not needed. Elemental copper can be recovered from the aqueous phase by electrolysis. The carboxylic acid can be recovered from the aqueous phase by, for example, distillation.

The following examples further illustrate this invention:

EXAMPLE 1

To 200 g of a mixture of chlorinated 4-methylmethylbenzoates (MMB) was added 33.8 g of propionic acid and 27.3 g of copper powder. After heating for 11 hr at 140 to 150° C., the mixture was cooled to 90° C. and diluted with 194 g of H$_2$O. Since there was unreacted copper present, the mixture was filtered. Two phases formed. The lower organic layer was washed with 1 13 9 of H$_2$O and then with 112 g of 9 wt % Na$_2$CO$_3$. The following table gives the composition of the substrate and product mixtures:

|  | Substrate Mixture (wt %) | Product Mixture (wt %) |
|---|---|---|
| 3-chloro MMB | 42.0 | 60.2 |
| 3,5-dichloro MMB | 35.3 | 39.4 |
| 2,5-dichloro MMB | 17.2 | 0.4 |
| 2,3-dichloro MMB | 1.3 | — |
| 2,3,5-trichloro MMB | 4.2 | — |

EXAMPLE 2

Example 1 was repeated using 62.5 g of propionic acid and 48.5 g of copper powder. After heating for 3 hr at 160° C., the mixture was cooled to 90° C. and diluted with 128 g of $H_2O$. Since there was unreacted copper present, the mixture was filtered. Two phases formed. The lower organic layer was washed with $H_2O$ and then with 100 g of 4 wt % $K_2CO_3$. The following table gives the composition of the substrate and product mixtures:

|  | Substrate Mixture (wt %) | Product Mixture (wt %) |
|---|---|---|
| 3-chloro MMB | 42.0 | 60.0 |
| 3,5-dichloro MMB | 35.3 | 39.6 |
| 2,5-dichloro MMB | 17.2 | 0.4 |
| 2,3-dichloro MMB | 1.3 | — |
| 2,3,5-trichloro MMB | 4.2 | — |

These examples show that not only is it possible to separate the desired product(s) from the copper salts and the organic acid by diluting with water, but that this method is preferably to precipitating out the copper salts, distilling the organic acid, and subsequently distilling the desired product.

We claim:

1. A method of isolating the aromatic product formed when a substrate having the general formula

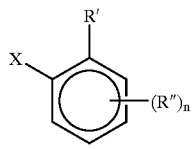

is dehalogenated, forming a product mixture of copper salts and said aromatic product comprising
   (A) adding water to said product mixture in an amount about 1 to about 5 times the amount of said substrate, whereby an organic phase forms that contains said aromatic product and an aqueous phase forms that contains said copper salts;
   (B) if the density of said organic phase differs from the density of said aqueous phase by less than 0.1 g/cc, adding a suitable solvent to said product mixture in an amount sufficient to increase the difference in density between said organic and aqueous phases to at least 0.1 g/cc; and
   (C) separating said organic phase from said aqueous phase, where X is the halogen removed from said substrate to form said product, R' is COOH, COOR, COR, CN, COH(R)$_2$, or SO$_3$H, each R" is independently selected from halogen, R, or OR or two vicinal R" groups form one or more fused aromatic rings, R is alkyl from $C_1$ to $C_{18}$ or aryl from $C_6$ to $C_{18}$, and n is 1 to 4.

2. A method according to claim 1 wherein X is chlorine.

3. A method according to claim 1 wherein R' is COOCH$_3$.

4. A method according to claim 1 wherein at least one R" is halogen.

5. A method according to claim 1 wherein at least one R" is methyl.

6. A method according to claim 1 wherein one R" is in the meta position.

7. A method according to claim 1 wherein n is 2.

8. A method according to claim 1 wherein said substrate is 2,3,5-trichloro-4-methylmethylbenzoate.

9. A method according to claim 1 wherein said carboxylic acid is acetic acid.

10. A method according to claim 1 wherein said carboxylic acid is propionic acid.

11. A method according to claim 1 wherein, in step (B), a denser solvent is added.

12. A method according to claim 11 wherein said solvent is selected from the group consisting of chloroform, dichloroethane, chlorobenzene, and mixtures thereof.

13. A method according to claim 1 wherein, in step (B), a less dense solvent is added.

14. A method according to claim 13 wherein said less dense solvent is selected from the group consisting of hexane, toluene, ethyl acetate, and mixtures thereof.

15. A method according to claim 1 wherein, in step (C), said phases are separated by decantation.

16. A method according to claim 1 including the additional steps of forming said product mixture by reacting said substrate with elemental copper and a carboxylic acid.

17. A method of isolating the aromatic product formed when a substrate having the general formula

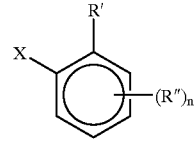

is dehalogenated, forming a product mixture of copper salts and aromatic product comprising
   (A) adding water to said product mixture in an amount about 1 to about 5 times the amount of said substrate, forming an organic phase that contains said aromatic product and an aqueous phase that contains said copper salts; and
   (B) separating said organic phase from said aqueous phase by decantation, where X is the halogen to be removed, R' is COOR, R is alkyl from $C_1$ to $C_4$, one R" is methyl and a second R" is a halogen in the meta position, and n is 2.

18. A method according to claim 17 wherein X is chlorine.

19. A method according to claim 17 wherein one R" is chlorine.

20. A method of isolating 3,5-dichloro-4-methylmethylbenzoate from a product mixture with cuprous chloride and a copper salt of a carboxylic acid selected from the group consisting of acetic acid, propionic acid, and mixtures thereof comprising
   (A) adding water to said 3,5-dichloro-4-methylmethylbenzoate in an amount about 1 to about 5 times the amount of said 3,5-dichloro-4-methylmethylbenzoate, forming an organic phase that contains said 3,5-dichloro4-methylmethylbenzoate and an aqueous phase that contains said cuprous chloride and said copper salt of a carboxylic acid in solution; and
   (B) separating said organic phase from said aqueous phase by decantation.

* * * * *